(12) United States Patent
Baier-Löwenstein et al.

(10) Patent No.: US 10,064,568 B2
(45) Date of Patent: Sep. 4, 2018

(54) DEVICE FOR DETERMINING THE REGIONAL DISTRIBUTION OF A PARAMETER FOR LUNG PERFUSION

(71) Applicant: Dräger Medical GmbH, Lübeck (DE)

(72) Inventors: Tim Baier-Löwenstein, Herrnburg (DE); Yvo Gärber, Breitenfelde (DE); Stefan Mersmann, Lübeck (DE); Eckhard Teschner, Lübeck (DE); Steffen Leonhardt, Aachen (DE); Robert Pikkemaat, Aachen (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 743 days.

(21) Appl. No.: 14/421,228

(22) PCT Filed: Aug. 8, 2013

(86) PCT No.: PCT/EP2013/066633
§ 371 (c)(1),
(2) Date: Feb. 12, 2015

(87) PCT Pub. No.: WO2014/029631
PCT Pub. Date: Feb. 27, 2014

(65) Prior Publication Data
US 2015/0216443 A1    Aug. 6, 2015

(30) Foreign Application Priority Data

Aug. 20, 2012 (DE) .................. 10 2012 214 786

(51) Int. Cl.
*A61B 5/05* (2006.01)
*A61B 5/053* (2006.01)
(Continued)

(52) U.S. Cl.
CPC .............. *A61B 5/0536* (2013.01); *A61B 5/08* (2013.01); *A61B 5/0813* (2013.01); *A61B 5/742* (2013.01);
(Continued)

(58) Field of Classification Search
None
See application file for complete search history.

(56) References Cited

U.S. PATENT DOCUMENTS

| 4,870,578 A | 9/1989 | Vysin et al. | |
| 5,807,321 A * | 9/1998 | Stoker ............... | A61M 5/16809 604/251 |

(Continued)

FOREIGN PATENT DOCUMENTS

| CN | 101801265 A | 8/2010 |
| DE | 693 20 173 T2 | 2/1999 |

(Continued)

OTHER PUBLICATIONS

Fagerbeg et al (Electrical impedance tomography applied to assess matching of pulmonary ventilation and perfusion in a porcine experimental model.*

(Continued)

*Primary Examiner* — Joel F Brutus
(74) *Attorney, Agent, or Firm* — McGlew and Tuttle, P.C.

(57) ABSTRACT

A device for determining the regional distribution of a parameter for lung perfusion includes an electrical impedance tomography unit with electrodes (E1, . . . EN), which can be placed on the thorax, that are connected to a control and analysis unit (2) and an administering device (4) for the intravenous administration of a conductivity contrast medium. The control and analysis unit (2) is configured to display changes in impedance distribution occurring as a consequence of the administration of conductivity contrast (Continued)

medium as a parameter for lung perfusion in the section plane as a function of time. The administering device (4) has a controllable dispensing device. The control and analysis unit and the dispensing device are connected with one another via a data link (3). A start time and an end time and a quantity of an administered bolus of the conductivity contrast medium are available to the control and analysis unit (2).

18 Claims, 13 Drawing Sheets

(51) Int. Cl.

| | | |
|---|---|---|
| *A61M 5/00* | (2006.01) | |
| *A61B 5/08* | (2006.01) | |
| *A61M 5/145* | (2006.01) | |
| *A61M 5/172* | (2006.01) | |
| *A61B 5/00* | (2006.01) | |
| *A61B 5/028* | (2006.01) | |

(52) U.S. Cl.
CPC .............. *A61B 5/746* (2013.01); *A61M 5/007* (2013.01); *A61M 5/1452* (2013.01); *A61M 5/1723* (2013.01); *A61B 5/028* (2013.01); *A61M 2205/3368* (2013.01); *A61M 2205/3576* (2013.01)

(56) References Cited

U.S. PATENT DOCUMENTS

| | | | |
|---|---|---|---|
| 8,808,193 | B2 | 8/2014 | Weiler |
| 2003/0216630 | A1 | 11/2003 | Jersey-Willuhn et al. |
| 2004/0133123 | A1 | 7/2004 | Leonhardt et al. |
| 2008/0119715 | A1 | 5/2008 | Gonzalez Molezzi et al. |
| 2008/0131362 | A1* | 6/2008 | Rousso .................. A61B 5/417 424/1.11 |
| 2008/0221464 | A1* | 9/2008 | Al-Ali .................. A61B 5/0261 600/500 |
| 2009/0118634 | A1 | 5/2009 | Weiler |
| 2010/0114064 | A1* | 5/2010 | Kalafut .................. A61B 5/411 604/508 |

FOREIGN PATENT DOCUMENTS

| | | |
|---|---|---|
| DE | 103 01 202 B3 | 1/2004 |
| DE | 696 30 245 T2 | 8/2004 |
| DE | 601 24 541 T2 | 9/2007 |
| DE | 10 2007 056 481 A1 | 5/2008 |
| EP | 0 619 716 B1 | 8/1998 |
| EP | 0 967 497 B1 | 10/2003 |
| EP | 1 292 224 B1 | 11/2006 |
| EP | 2 228 009 A1 | 9/2010 |

OTHER PUBLICATIONS

Gawlinski (Measuring cardiac output: Intermittent bolus themodilution method).*

Frerichs et al (Regional lung perfusion as determined by electrical impedance tomography in comparison with electron beam CT imaging).*

"Determination of Lung perfusion by Means of Electrical Impedance Tomography" by H. Luepschen et al., 44th Annual Conference of the German Society of Biomedical Engineering (BNT 2010), Rostock, Germany, Oct. 6-8, 2010.~.

"Dynamic separation of pulmonary and cardiac changes in electrical impedance tomography," Physiol Meas, Jun. 2008; 29(6), pp. 1-14.

"A survey of image registration techniques" by L. G. Brown in ACM computing surveys, vol. 24, No. 4, 1992, pp. 325-376.

"Numerical methods for image registration," J. Modersitzki, Oxford University Press, 2004).

"The shape of indicator dilution curves used for cardiac output measurement in man," D. M. Band et al., The Journal of Physiology, Jan. 1, 1997, 498 (Part 1), 225-229.

"Automatic gait recognition by symmetry analysis,", M. S. Nixon, Pattern Recogn. Lett., 24(13), 2175-2183, 2003.

"Detection of partial symmetry using correlation with rotated-reflected images," Masuda et al., Pattern Recognition, 26 (8); 1245-1253, 1993).

Inéz Frerichs et al: "Regional Lung Perfusion as Determined by Electrical Impedance Tomography in Comparison With Electron Beam CT Imaging", IEEE Transactions on Medical Imaging, IEEE Service Center, Piscataway, NJ, US, vol. 21, No. 6, Jun. 1, 2002 (Jun. 1, 2002), XP011076301, ISSN: 0278-0062 abstract 'I. Introduction' 'II. Methods'.

Fagerberg Anneli et al: "Electrical impedance tomography applied to assess matching of pulmonary ventilation and perfusion in a porcine experimental model", Critical Care, Biomed Central Ltd., London, GB, vol. 13, No. 2, Mar. 5, 2009 (Mar. 5, 2009), p. R34, XP021053506, ISSN: 1364-8535, DOI: 10.1186/CC7741 abstract 'Introduction' 'Materials and methods'.

Eckhard Teschner et al: "Electrical Impedance Tomography: The realization of regional ventilation monitoring", Jan. 1, 2011 (Jan. 1, 2011), XP055087286, Retrieved from the Internet: URL: https://web.archive.org/save/http://www.draeger.net/media/10/08/98/10089883/rsp_eit_booklet_9066788 en.pdf.

* cited by examiner

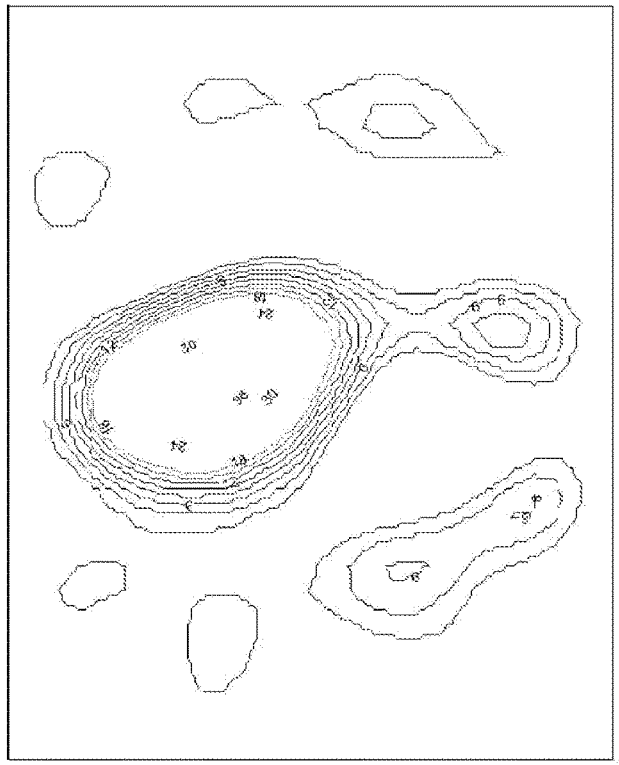
Fig. 5
Lung Perfusion 1.275 Sec After Bolus Administration
Lung Perfusion 0.025 Sec After Bolus Administration

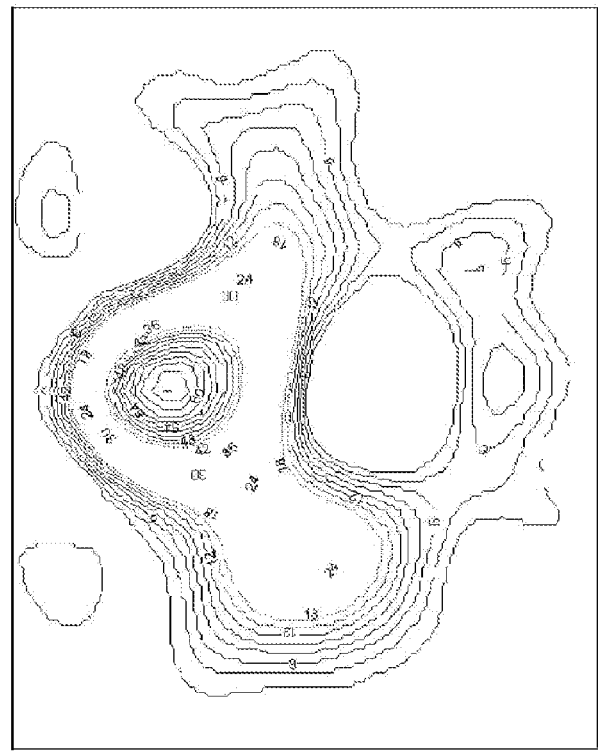
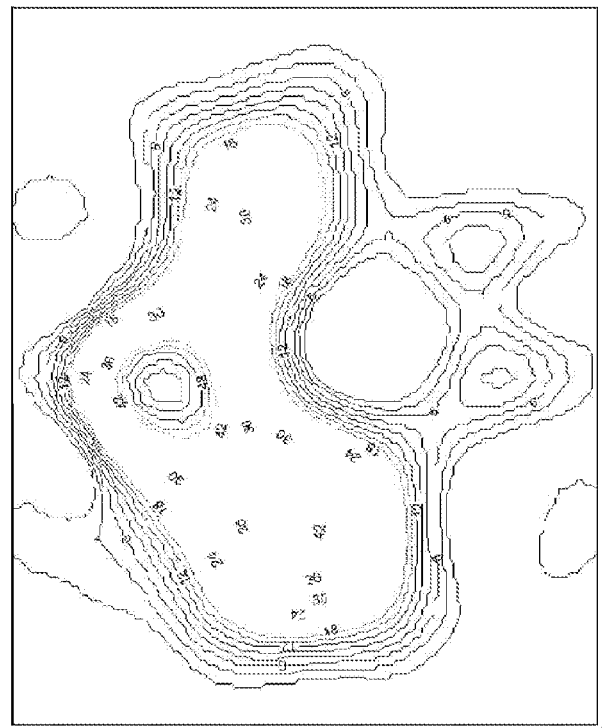
Fig. 6

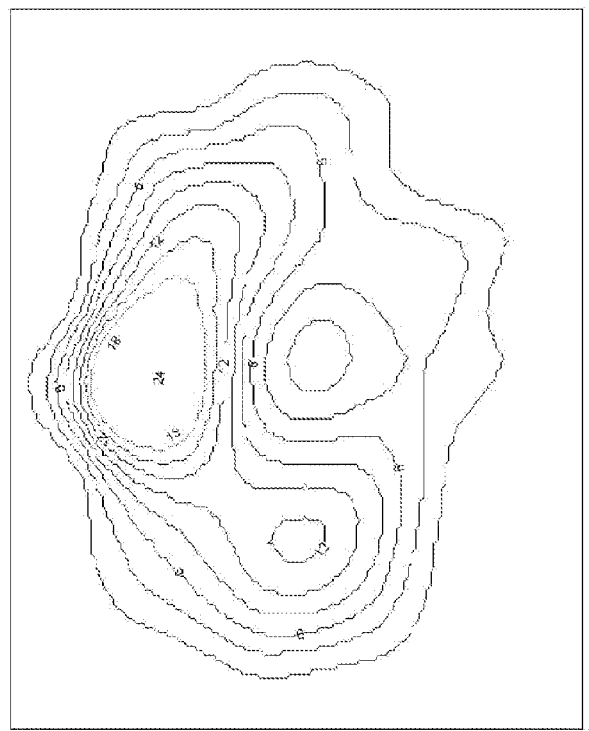
Lung Perfusion 10.025 Sec After Bolus Administration
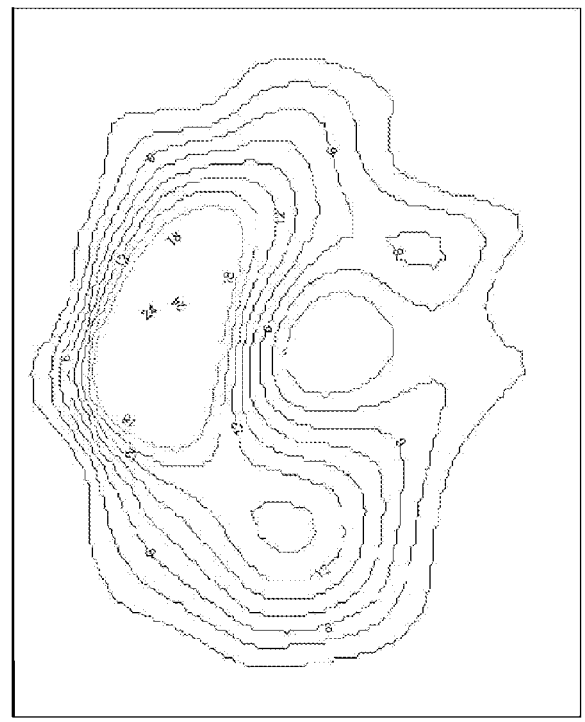
Lung Perfusion 8.775 Sec After Bolus Administration
Fig. 8

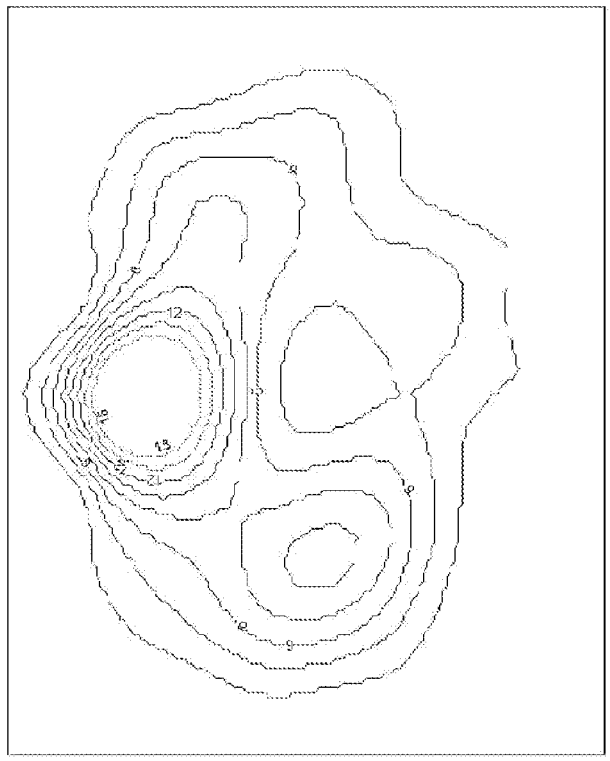
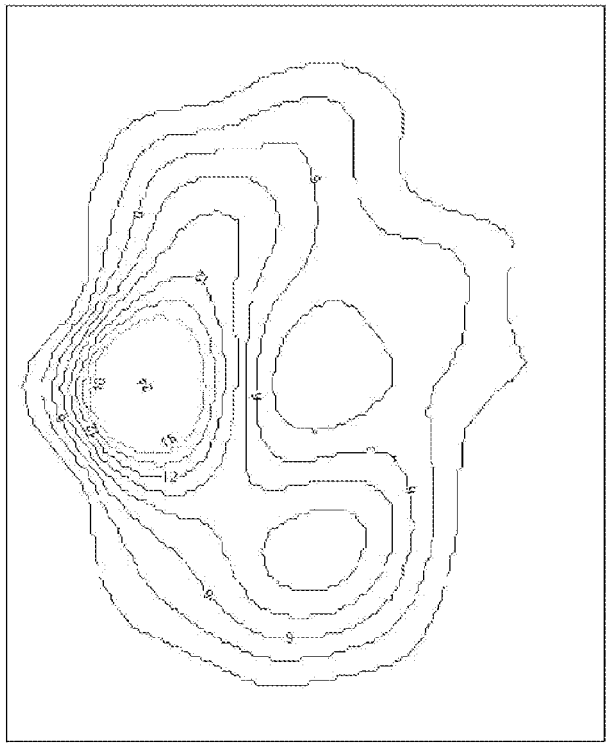
Fig. 9
Lung Perfusion 12.525 Sec After Bolus Administration
Lung Perfusion 11.275 Sec After Bolus Administration Lung Perfusion 13.775 Sec After Bolus Administration   Lung Perfusion 15.025 Sec After Bolus Administration   Fig. 10

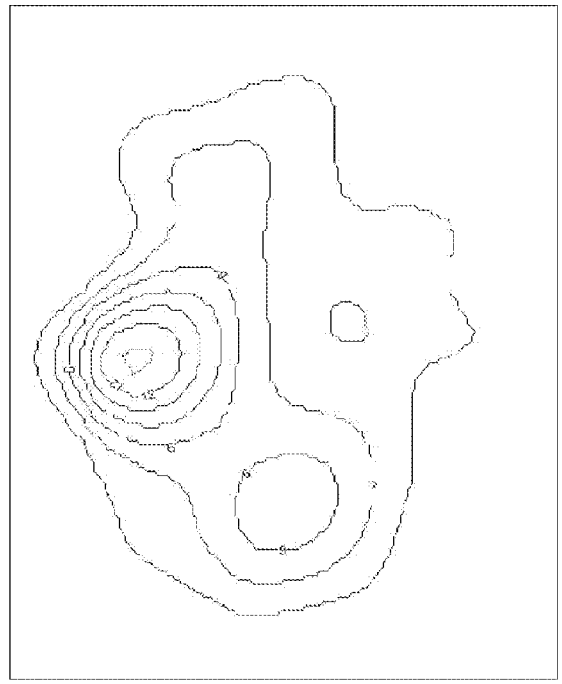
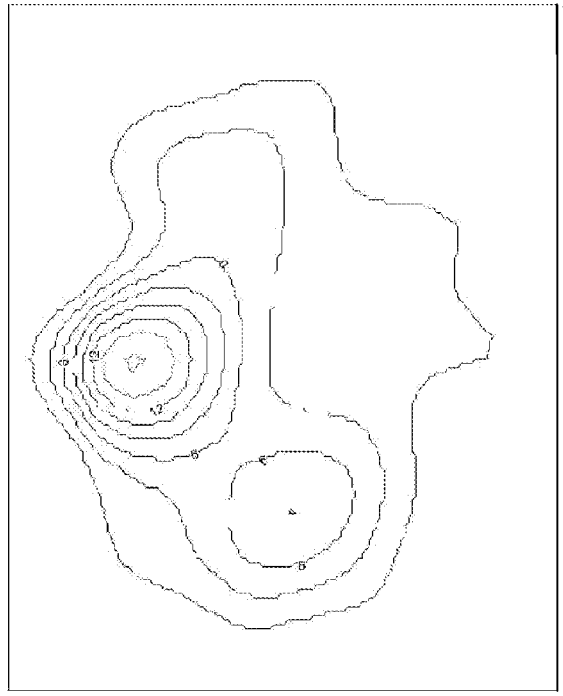
Fig. 12
Lung Perfusion 20.025 Sec After Bolus Administration
Lung Perfusion 18.775 Sec After Bolus Administration Lung Perfusion 21.275 Sec After Bolus Administration

DEVICE FOR DETERMINING THE REGIONAL DISTRIBUTION OF A PARAMETER FOR LUNG PERFUSION

CROSS REFERENCE TO RELATED APPLICATIONS

This application is a United States National Phase Application of International Application PCT/EP2013/066633 filed Aug. 8, 2103 and claims the benefit of priority under 35 U.S.C. § 119 of German Patent Application DE 10 2012 214 786.1 filed Aug. 20, 2012, the entire contents of which are incorporated herein by reference.

FIELD OF THE INVENTION

The present invention pertains to a device for determining the regional distribution of a parameter for lung perfusion in a section plane of a patient's thorax with an electrical impedance tomography unit with a plurality of electrodes, which can be placed on the thorax distributed around the circumference of the section place, and with a control and analyzing unit, which is connected with a plurality of electrodes and which is set up to successively feed alternating current or alternating voltage to each pair of electrodes and to record voltage or current signals of the other electrodes as measured signals and to reconstruct the impedance distribution in the section place from the measured signals, and with an administering device for the intravenous administration of a conductivity contrast medium, wherein the control and analysis unit is further set up to display the changes in the impedance distribution occurring as a consequence of the administration of conductivity contrast medium as a parameter for lung perfusion in the section plane as a function of time.

BACKGROUND OF THE INVENTION

Such a device is known from the article "Determination of Lung Perfusion by Means of Electrical Impedance Tomography," Henning Luepschen et al., Biomed Tech 2010; 55 (Suppl. 1). The device has an electrical impedance tomography unit (EIT unit), as it is frequently used in medical engineering applications. Such an EIT unit has a plurality of electrodes, which can be placed on the thorax distributed around the circumference of a section plane. Furthermore, a control and analysis unit is present, which is connected with the electrodes and is set up to consecutively feed alternating current or alternating voltage to each pair of the plurality of electrodes and to record the resulting voltage or current signals of the other electrodes as measured signals and to reconstruct the impedance distribution in the section plane from the measured signals. More precisely, what is determined in this case is not the impedance in its absolute value but its change compared to a reference distribution. Such an EIT unit is described, for example, in EP 2 228 009 A1.

Further, a manually operated administering device (e.g., a syringe) is present in the prior-art device for the intravenous administration of a conductivity contrast medium. Liquids whose conductivity differs markedly from that of blood may be used as conductivity contrast media. After administering a bolus of the conductivity contrast medium, regional conductivity dilution curves can be recorded, i.e., the flow of the bolus through the section plane is manifested in a rapid rise in the impedance to a maximum, which is followed by a slower drop to the baseline (if the conductivity contrast medium lowers the impedance, a drop in impedance to a minimum and then a rise to the baseline are seen). Such dilution curves can be recorded for the individual image elements of the reconstructed impedance distribution of the section plane through the thorax and displayed on a display device. The instantaneous determined impedance values can be represented in a spatially resolved manner, for example, in a two-dimensional representation, the instantaneous values being represented by corresponding brightness values. After administering a bolus of the conductivity contrast medium, the inflow of the contrast medium into the right side of the heart, where a correspondingly increased brightness is seen as a result in the image of the section plane of the thorax in the area of the right heart, is then seen at first, for example, after which the contrast medium leaves the right side of the heart in the direction of the lungs, as a result of which the right parts of the heart, which are at first visualized with increased brightness, will again become darker and the lungs become brighter, after which the control medium will then flow back into the left side of the heart, which will then appear with a correspondingly increased brightness on the display device. Instead of a representation of the instantaneous impedance values, which varies over time, it is also possible to display other parameters of the dilution curves in a spatially resolved manner, for example, the maximum amplitude of the dilution curves or the integral value over the dilution curve; an individual, spatially resolved representation of a parameter for lung perfusion would then be generated in the latter cases for the administration of a bolus of the conductivity contrast medium. The term "parameter for lung perfusion" is used here to make it clear that the lung perfusion values do not have to be determined here in terms of their absolute values, but the relative percentages relative to the overall perfusion may be sufficient.

When measuring the lung perfusion with the use of a conductivity contrast medium, the contrast medium must first be injected in order to subsequently start the perfusion measurement on the EIT unit. Two problems arise from this when a measurement is carried out: a) Relative to the administration of the contrast medium, and b) relative to the lung perfusion measurement.

When administering the conductivity contrast medium, the rate at which the contrast medium is administered may sometimes greatly affect the accuracy of the measurement and the comparability of different measurements with one another. This is especially true if the contrast medium is administered manually without determining the exact volume and/or the exact point in time. Insofar as the administration of the contrast medium is performed manually and without technical monitoring, the in vivo concentration of the contrast medium cannot be assumed to be comparable for all measurements, and the quantifiability and comparability of EIT analyses is not consequently guaranteed.

A time shift also arises during the lung perfusion measurement between the administration of the conductivity contrast medium and the start of the measurement. This time shift may already lead to impaired quality of the analytical results. Since, moreover, the time shift cannot be assumed to be always constant, two measurements are comparable with one another only conditionally, because different concentrations of the contrast medium in the blood can be assumed to occur at the respective measurement times. This also applies to the end of the administration of the contrast medium, since the lung perfusion measurement also must be terminated now after a defined time. A time shift between the end of the administration of the contrast medium and the termination of the EIT measurement can be assumed here as well.

Since the measurements may possibly deviate greatly from one another in case of manual administration of the conductivity contrast medium and the results of the measurements are not reproducible, no reliable conclusions can be drawn from the measured values. For example, it is not possible to determine the ventilation-perfusion ratio (V/Q ratio) such that different measurements would be comparable with one another and a trend could thus be detected.

SUMMARY OF THE INVENTION

An object of the present invention is to design a device for determining the regional distribution of a parameter for lung perfusion such that better reproducibility and comparability of consecutive measurements on one person or of measurements on different persons can be achieved.

According to the present invention, a device for determining the regional distribution of a parameter for lung perfusion in a section plane of the thorax is provided with an electrical impedance tomography unit. The electrical impedance tomography unit includes a plurality of electrodes, which can be placed on the thorax distributed around the circumference of the section plane, and includes a control and analysis unit, which is connected with the plurality of electrodes and is set up (configured) to consecutively feed alternating current or alternating voltage to each pair of electrodes to record voltage or current signals of the other electrodes as measured signals and to reconstruct the impedance distribution in the section plane from the measured signals. The device also includes an administering device for the intravenous administration of a conductivity contrast medium. The control and analysis unit is further set up to display the changes in the impedance distribution occurring as a consequence of the administration of conductivity contrast medium as a parameter for lung perfusion in the section plane as a function of time. The administering device for the conductivity contrast medium has a controllable dispensing device. The control and analysis unit and the dispensing device are connected with one another via a data link and are set up such that at least the start time and the end time as well as the quantity of an administered bolus of the conductivity contrast medium are available as parameters to the control and analysis unit. This, of course, also comprises parameter sets that are obtained by conversion, for example, the start time, quantity and rate of injection or start time, quantity and duration of the injection, etc. The control and analysis unit may be set up in this case to send a preset start time, a preset quantity and a preset time course of the infusion of the conductivity contrast medium as control parameters to the controllable dispensing device via the data link. As an alternative, the control and analysis unit may only start the dispensing device and receives the exact start time, quantity and time course of the infusion of the conductivity contrast medium as feedback from the dispensing device. As an alternative, the controllable dispensing device may also be actuated directly or indirectly by third or outside devices (e.g., respirator or monitor) via the control and analysis unit, in which case the dispensing device will send data pertaining to the start time, quantity administered and time course of the bolus administration to the control and analysis unit. The data communication via the data link may be either a wired or wireless communication data link.

In a preferred embodiment, the control and analysis unit is set up, further, to repeat the administration of the bolus of the conductivity contrast medium at preset time intervals and to display the changes over time in the parameter of the lung perfusion as a function of the trend graph representing the time. As an alternative, the administration of the bolus may be triggered manually by actuating a switch, in which case the actuation of the switch causes the dispensing device to administer the bolus of the conductivity contrast medium, the dispensing device being started either by the control and analysis unit, to which the preset parameters (start, quantity and time course of the bolus administration) are known in this case, or indirectly, without the intermediary of the control and analysis unit, in which case the dispensing device is set up then to send said parameters of the bolus administration to the control and analysis unit.

As an alternative, the repeated actuation of the controllable dispensing device at preset time intervals may also be performed by third devices (e.g., respirator or monitor) directly or indirectly via the control and analysis unit.

In a preferred embodiment, the control and analysis unit is further set up to display the parameter for the perfusion two-dimensionally in a spatially resolved manner over the lung surface in the section plane through the thorax.

In another preferred embodiment, the control and analysis unit is further set up to determine the perfused surface in the section plane and to display perfused surfaces, which are obtained from the respective administrations of a bolus of the conductivity contrast medium, as a trend graph as a function of the time of administration of the boli of the conductivity contrast medium. Areas in which the parameter for the perfusion is above a preset threshold value may be defined as perfused surfaces. In addition, a parameter for the homogeneity of the perfusion, e.g., the mean deviation from the mean perfusion in the perfused surface (=0 if the perfusion is equal everywhere), can be determined within the perfused surfaces and displayed as a trend graph as a function of the time of bolus administrations.

In a preferred embodiment, the control and analysis unit is further set up to determine the regional distribution of ventilation during times without administration of conductivity contrast medium from the impedance distributions of the section plane of the thorax and to display it as a function of time. Procedures for determining the intratidal distribution of ventilation over the cross section of the lung are described, for example, in EP 2 228 009 A1.

In a preferred embodiment, the dispensing device is provided with a temperature sensor for the conductivity contrast medium or with a temperature-regulating device for the conductivity contrast medium, which can be controlled by the control and analysis unit. The control and analysis unit is set up to determine the cardiac output volume from the temperature of the conductivity contrast medium, which was determined or set by the temperature-regulating device, on the basis of the dilution principle, and to calibrate the parameter for the lung perfusion in absolute terms on the basis of the cardiac output volume determined. In principle, an isotonic solution, which does not cause any change in conductivity and is not consequently a conductivity contrast medium proper, may also be used for the calibration.

By measuring or setting the temperature of the conductivity contrast medium, it is possible to calculate the cardiac output volume by means of the dilution principle (for example, according to the Steward-Hamilton method) and thus to calibrate the measured EIT values with respect to the perfusion and to improve the accuracy of the measurement.

It is possible with the present invention to increase the accuracy of the measurement and to guarantee the comparability of different measurements, to make it possible to carry out cyclic, automatic measurements, and to reduce the possibilities of incorrect operation by the user.

The administration of the conductivity contrast medium is carried out under defined conditions, so that the start time, the volume and the rate of injection are known to the control and analysis unit. The control and analysis unit triggers the administration of a bolus of the conductivity contrast medium with known parameters, either as a consequence of the actuation of a switch or at preset time intervals, automatically or triggered by external third devices (e.g., respirator or monitor), and the EIT unit is triggered to perform repeated measurements of the regional impedance distributions in the section plane of the thorax. As an alternative, the dispensing device sends data concerning the start time, quantity and time course of the administration of a bolus to the control and analysis unit if the dispensing device is triggered to administer a bolus either directly or by an external device.

The time course of a perfusion measurement is accurately defined due to the data link between the control and analysis unit of the EIT unit and third devices and the dispensing device and by the control or synchronization of the EIT unit and the dispensing device. A defined volume of a conductivity contrast medium may be administered under defined conditions and a corresponding EIT measurement may be triggered by the EIT unit at regular time intervals for a continuous perfusion measurement. The accuracy of the measurement is increased hereby and comparability of different measurements is guaranteed. If, moreover, a timer is integrated in the device, cyclical, automatically performed measurements are possible. The sources of error of a possible incorrect operation by the user are reduced, because the user can start a corresponding maneuver by pressing a single switch. Unlike in the state of the art, the user does not therefore have to inject the conductivity contrast medium any more, to trigger the EIT measurement and possibly stop it. Therefore, the operation of such a device is also substantially simpler.

Due to the defined administration of boli, a precise baseline can be determined for the EIT measurement on the basis of a modified Steward-Hamilton method. The method may also be considered to be a Steward-Hamilton method for the EIT measurement. Not only the temperature of the injectate, but also the changed conductivity in the blood are measured here. Such a method is described in: "Determination of Lung perfusion by Means of Electrical Impedance Tomography" by H. Luepschen et al., 44th Annual Conference of the German Society of Biomedical Engineering (BNT 2010), Rostock, Germany, Oct. 6-8, 2010.

Since the results of the EIT measurements can be compared with one another, a trend over the cardiac minute volume and/or the lung perfusion can be calculated and displayed. The calculation and display may take place both in the form of a regional graph, similarly to an EIT ventilation image, but also as an individual measured value (scalar representation).

The ratio of local ventilation V to perfusion Q must be as balanced as possible for the best possible gas exchange in the lung. The ratio V/Q=0.8 . . . 1.0 is therefore considered to be optimal in the literature. However, there is no possibility so far for determining this ratio regionally in real time. The V/Q ratio can now also be determined and displayed both in a spatially resolved form and as an individual measured value (scalar) due to the above-described improvement of the measurement results within the framework of the present invention and the quantitative interpretation thereof in reference to the physiological parameters. A comparison of intraindividual and interindividual data is likewise possible now. A trend concerning the V/Q ratio can thus also be determined and displayed and used as a parameter for diagnosis and therapy. Based on a defined V/Q ratio, the respiration parameters can now also be optimized for a patient, so that the most optimal V/Q ratio possible is obtained. The optimal respiration parameters can be determined in various manners. They may be set either by a physician or health care staff, or they are determined by another system (e.g., an expert system) and proposed to the physician, or they are determined and automatically applied by another system (e.g., an expert system). To exchange the EIT perfusion data determined and the regional V/Q ratio values with the respirator or the additional system (e.g., an expert system), there may be a data link between the control and analysis unit and the additional system (e.g., expert system) or the respirator.

Moreover, the administration of drugs can also be optimized on the basis of a defined V/Q ratio, so that the most optimal V/Q ratio possible is obtained. They may be set either by a physician or health care staff, or they are determined by an expert system and proposed to the physician, or they are determined and automatically applied by an additional system (e.g., an expert system).

A new field of application emerges for EIT due to the controlled use of conductivity contrast media. The regional determination and quantification of shunts (lung areas that are perfused with blood but are not ventilated) and dead spaces (lung areas that are ventilated but are not perfused with blood) is not readily possible with the conventional "difference-in-time" EIT. This diagnostically and therapeutically relevant regional evaluation is possible, in principle, by means of the device according to the present invention. Corresponding trends can also be calculated and visualized by means of the shunts and dead spaces of the lung. If shunts or dead spaces are determined, corresponding therapeutic recommendations can also be outputted based on this by the control and analysis unit or sent to the additional system (e.g., an expert system) or the respirator.

By means of the defined administration of boli at certain time intervals, it is possible to perform a "calibration" of the information determined by the cardiac output and blood perfusion, which information is determined by means of a method, for example, that described in "Dynamic separation of pulmonary and cardiac changes in electrical impedance tomography,", Physiol Meas, June 2008; 29(6), pp. 1-14. The accuracy of the results can be further improved if this procedure is combined with a dilution measurement. If marked changes are seen in cardiovascular data, a change in lung perfusion or stroke volume can be inferred from this and a corresponding alarm can be generated.

It applies to all the above-mentioned measured values and trends that a corresponding alarm management may be provided. For example, alarms may be triggered in case of a correspondingly large shunt or dead space. The alarm limits eliciting triggering may either be entered here on the device by the user or they are generated automatically on the basis of corresponding clinical guidelines by an additional system (e.g., an expert system). An alarm may also be triggered in case of a corresponding change, i.e., as a function of the gradient of the observed measured value.

It is also possible now with the improvements of the measured values that are made possible by the device according to the present invention to carry out an image registration (cf., for example, "A survey of image registration techniques" by L. G. Brown in ACM computing surveys, Vol. 24, No. 4, 1992, pp. 325-376, "Numerical methods for image registration," J. Modersitzki, Oxford University Press, 2004) and to insert the image information obtained by means of the EIT on lung perfusion and ventilation, for example, into a computed tomogram and thus to link the two modalities (CT and EIT) with one another. It is possible, as a result, for physicians and health care staff to diagnose clinical pictures more efficiently and to adapt the therapy correspondingly.

It is also possible due to the improvement of the measured values to record a multi-slice EIT image of the lung perfusion by placing the electrode ring consecutively at different levels around the thorax and by carrying out corresponding measurements (or it is also possible to use directly an electrode array in which the electrodes are arranged in a plurality of rings around the thorax), so that a plurality of tomograms are obtained at different levels. These tomograms can be combined thanks to the results, whose accuracy is improved, so that a three-dimensional image of the lung can be prepared from this. If the measurement is repeated, the change in lung perfusion over time can be visualized three-dimensionally as a trend.

It is also possible due to the improved determination of the lung perfusion to recognize possible pathologies from the distribution of the bolus over the lung over time, on the one hand, by means of a symmetry operator ("The shape of indicator dilution curves used for cardiac output measurement in man," D. M. Band et al., The Journal of Physiology, 1997, Jan. 1, 498 (Part 1), 225-229, "Automatic gait recognition by symmetry analysis,", M. S. Nixon, Pattern Recogn. Lett., 24(13), 2175-2183, 2003, and "Detection of partial symmetry using correlation with rotated-reflected images," Masuda et al., Pattern Recognition, 26(8); 1245-1253, 1993). It is also possible to apply this symmetry operator to the distribution of the amplitude maxima in the tomogram in order to make it likewise possible to recognize possible pathologies. The symmetry operator calculates here the symmetry on the above-mentioned images and determines the symmetry between the right and left halves of the lung. The symmetry axis is not placed for this simply into the center of the image, but it is determined automatically, for example, such that the center of the cardiac region is determined automatically. However, it is also possible that the user defines a corresponding symmetry axis. A score can be calculated by means of the symmetry operator. The lower this score, the weaker is the symmetry between the two halves of the lung, and the higher is the probability of a lung disease. If the inverse of the symmetry operator is considered, the probability of a lung disease increases with increasing inverse of the score.

In a preferred embodiment, the control and analysis unit is further set up to identify lung areas in which the determined ventilation is above a preset threshold value and the determined perfusion is below another, preset threshold value as dead spaces and to display these in the shown tomogram of the lung.

In another preferred embodiment, the control and analysis unit is further set up to determine lung areas in which the perfusion is above a preset threshold value and the ventilation is below another, preset threshold value as shunts and to display them in the tomogram of the lung. In advantageous embodiments, the control and analysis unit may further be set up to display the changes in recognized shunts or dead spaces over time as a trend graph over a time period.

The present invention will be described below on the basis of an exemplary embodiment shown in the figures. The present invention shall be explained in more detail on the basis of the following figures and exemplary embodiments, without the present invention being limited to these. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 5 is a view showing the changes in the impedance distributions in the section plane through the thorax in the form of contour lines at consecutive times following the administration of the bolus;

FIG. 6 is another view showing the changes in the impedance distributions in the section plane through the thorax in the form of contour lines at consecutive times following the administration of the bolus;

FIG. 8 is another view showing the changes in the impedance distributions in the section plane through the thorax in the form of contour lines at consecutive times following the administration of the bolus;

FIG. 9 is another view showing the changes in the impedance distributions in the section plane through the thorax in the form of contour lines at consecutive times following the administration of the bolus;

FIG. 12 is another view showing the changes in the impedance distributions in the section plane through the thorax in the form of contour lines at consecutive times following the administration of the bolus.

DESCRIPTION OF THE PREFERRED EMBODIMENTS

Figure 1:
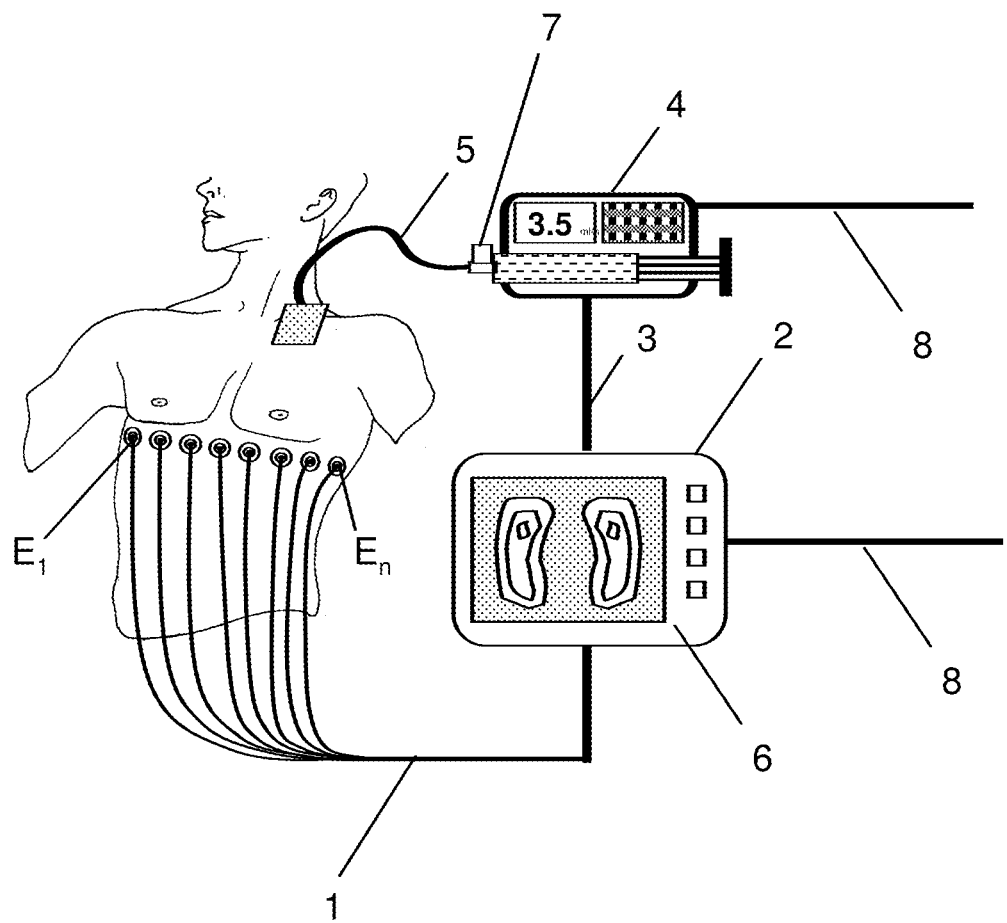
FIG. 1 is a schematic block diagram of the device according to the present invention.

Referring to the drawings, FIG. 1 shows the EIT unit connected to a control and analysis unit 2 by means of measuring cables 1. The administering device 4 is a controllable dispensing device. There is a bidirectional data link 3 between the control and analysis unit 2 and the administering device 4. The dispensing device 4 is connected with a venous catheter 5, via which the conductivity contrast medium is injected. The measuring cables 1 connect the control and analysis unit 2 with electrodes E1, ... EN, which are arranged around the thorax in a ring-shaped pattern. The control and analysis unit is provided with a display device 6. Both the administering device 4 and the control and analysis unit 2 may be connected via an external data link 8 with third devices, e.g., a respirator incl. an expert system contained therein or a monitor.

Figure 2:
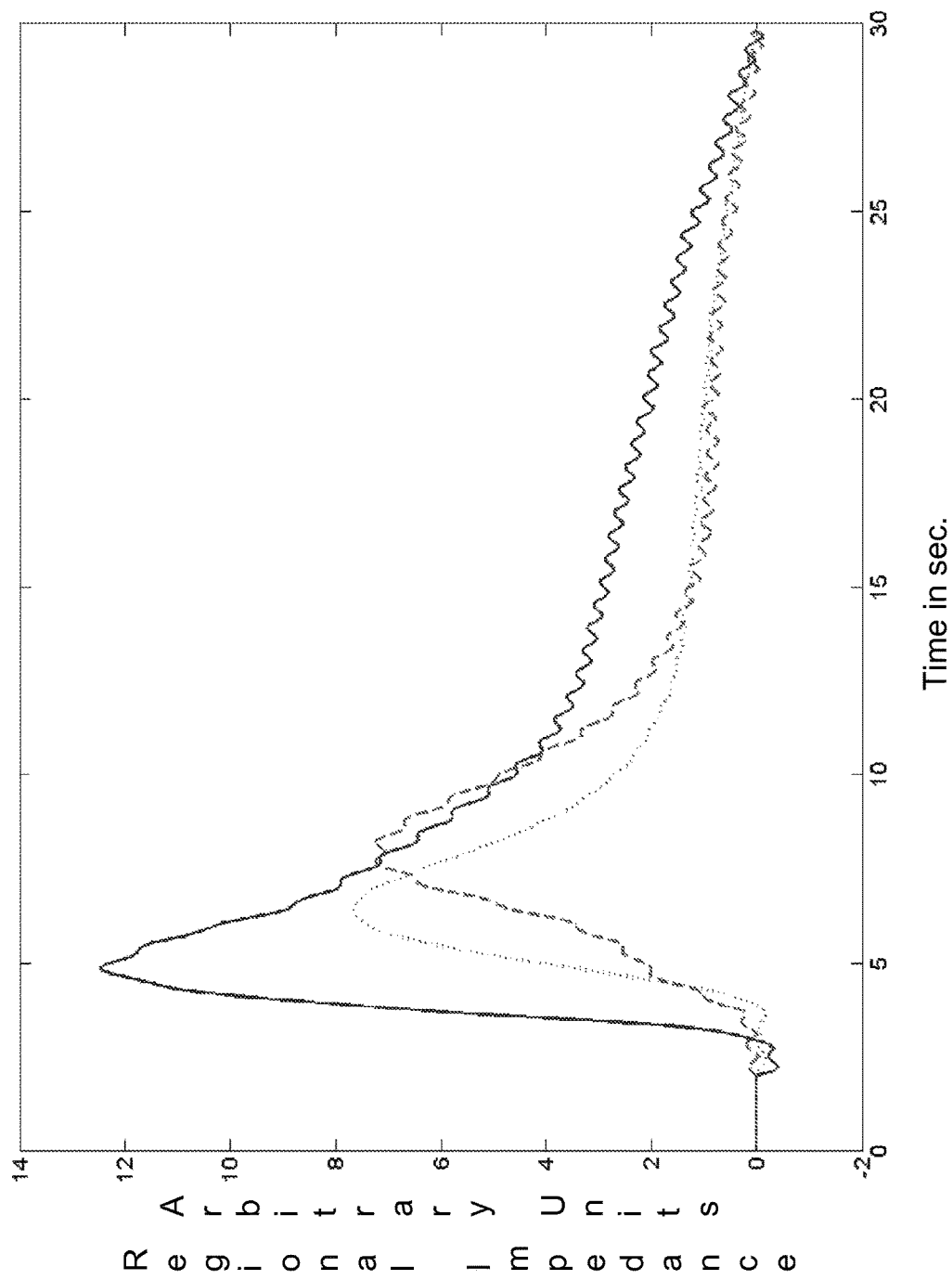
FIG. 2 is graph showing changes in impedance determined by EIT at three image points in the section plane through the thorax following administration of a bolus of the conductivity contrast medium.

An example of the function of the device according to the present invention during the administration of a conductivity bolus will be described below. The control and analysis unit triggers the dispensing device to inject a bolus of 10 mL of a 1-molar NaCl solution over a period of less than 2 sec via a central venous catheter. This bolus can be observed in the EIT image in the area of the heart after about 3 sec for about 25 sec and in the lung after about 6 sec for about 20 sec, and the maximum of the bolus can be observed after about 4 sec to 7 sec. For example, the impedance curves are shown in FIG. 2 following administration of a bolus at three points in the image plane of the thorax (here in the animal experiment, young pig weighing approx. 35 kg), where the solid curve corresponds to an image element in the area of the heart, the curve drawn in dotted line to an image element in the right lung and the curve drawn in broken line to an image element in the left lung. As can be determined from the curves in FIG. 2, the bolus reaches at first the heart and then the two lungs. A possible pathology in the lung can already be inferred in this case from the delay of the two lung curves in relation to one another. The time difference between the two halves of the lung can be used now to assess and display the degree of severity of the pathophysiological manifestation. The time difference of the curves for the right and left lungs is approx. 3 sec in this case. This time difference is determined from the time interval between the maxima of the two curves.

The measuring accuracy of the method is especially high during the time during which the bolus acts, because the bolus has a direct effect on the impedance of the blood and thus it affects the EIT measurement directly. Concerning the shape of the dilution curves as shown in FIG. 2, reference is made to the article "The shape of indicator dilution curves used for cardiac output measurement in man," D. M. Band et al., The Journal of Physiology, 1997, Jan. 1; 498 (Part 1), pp. 225-229. Due to the coupling of the EIT unit and the dispensing device in the device according to the present invention, the time sequence of the maneuvers can be coordinated such that a measurement of the lung perfusion is started as soon as the administration of the bolus is started. The measurement is checked on the basis of the knowledge of the above-described timing such that measurement is performed only over the time window in which the bolus acts. The results of this EIT measurement can be represented as lung perfusion after corresponding processing, for example, according to the method as described in the article "Dynamic separation of pulmonary and cardiac changes in electrical impedance tomography" by Deibele et al., Physiol. Meas., June 2008, 29(6), pp. 1-14. If the bolus measurement described is also combined with a thermodilution measurement, it is possible, moreover, the accurately determine the cardiac output volume at the time of the bolus measurement and to correlate this value with the value measured by means of EIT, so that the absolute stroke volume can be subsequently determined by means of the EIT.

Figure 3:
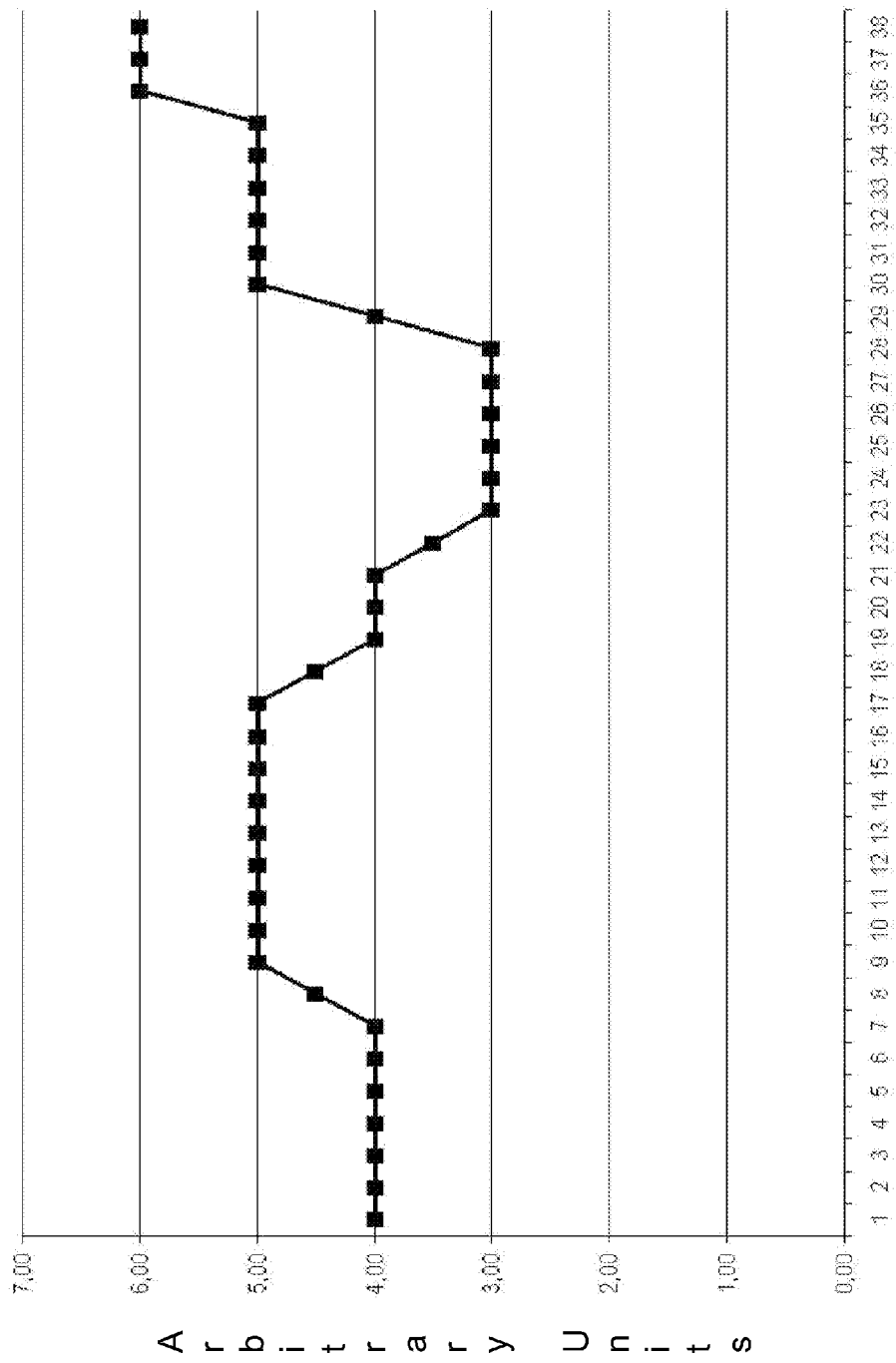
FIG. 3 is a graph showing a determined parameter for lung perfusion as a function of time as a trend graph.

FIG. 3 shows a parameter for lung perfusion, here the mean perfusion over the section plane through the thorax as a trend graph as a function of time over many hours. Such a trend graph of lung perfusion can provide important information on changes and the status of the patient.

Figure 4:
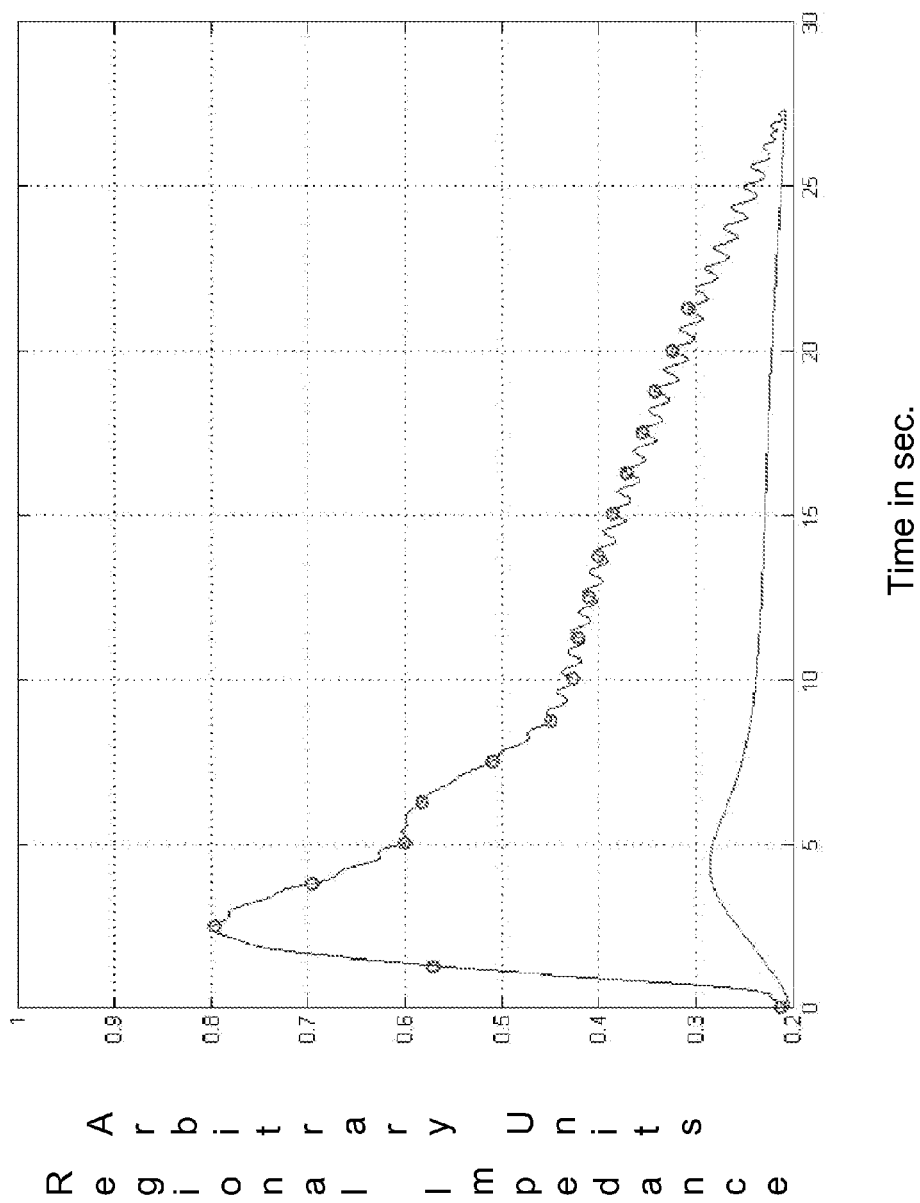
FIG. 4 is a graph showing impedance changes determined by EIT at two image points in the section plane through the thorax following administration of a bolus as a function of the time.

FIG. 4 shows the changes in the impedance determined by EIT at two image points in the section plane through the thorax following the administration of a bolus of the conductivity contrast medium as a function of time. The impedance distributions in the section plane through the thorax are shown in FIG. 5 through FIG. 14 in the form of contour lines at the times marked by circles.

FIG. 5 shows diagrams of lung perfusion by means of EIT as contour lines resolved at the time of 0.025 sec (the bolus has not yet arrived in the area of the heart and lung) following bolus administration as well as 1.275 sec after bolus administration. The bolus is seen in arriving in the cardiac region at 1.275 sec.

FIG. 6 shows diagrams of lung perfusion by means of EIT as contour lines resolved at the time of 2.525 sec and 3.775 sec after bolus administration. The bolus is seen flowing into the right lung at 2.525 sec. In addition, the left lung is also reached by the bolus at least partially. It is seen at 3.775 sec how the bolus propagates further over the two halves of the lungs.

Figure 7:
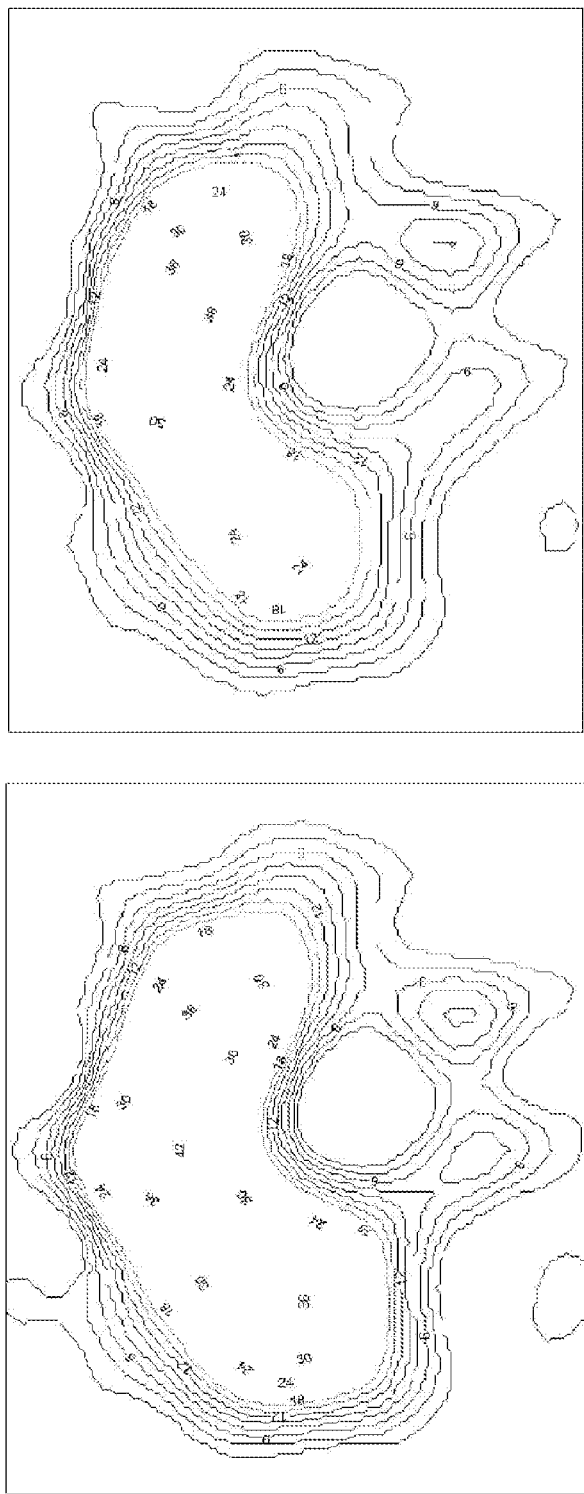
FIG. 7 is another view showing the changes in the impedance distributions in the section plane through the thorax in the form of contour lines at consecutive times following the administration of the bolus.
Figure 10:
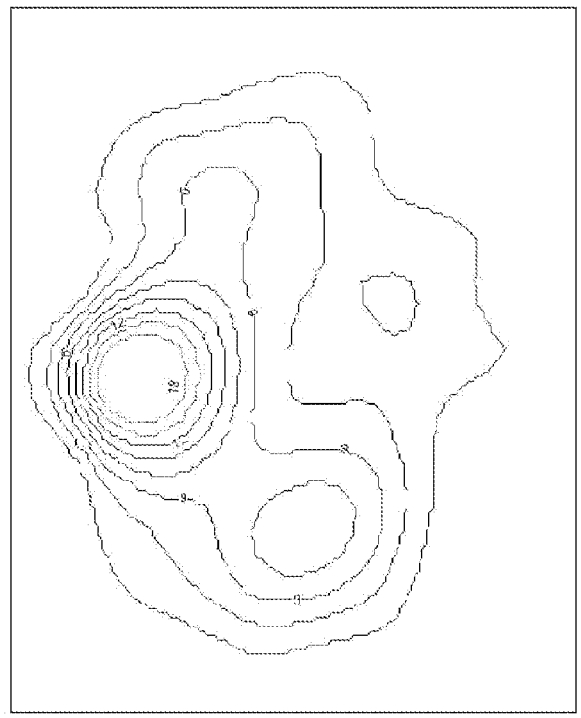
FIG. 10 is another view showing the changes in the impedance distributions in the section plane through the thorax in the form of contour lines at consecutive times following the administration of the bolus.
Figure 11:
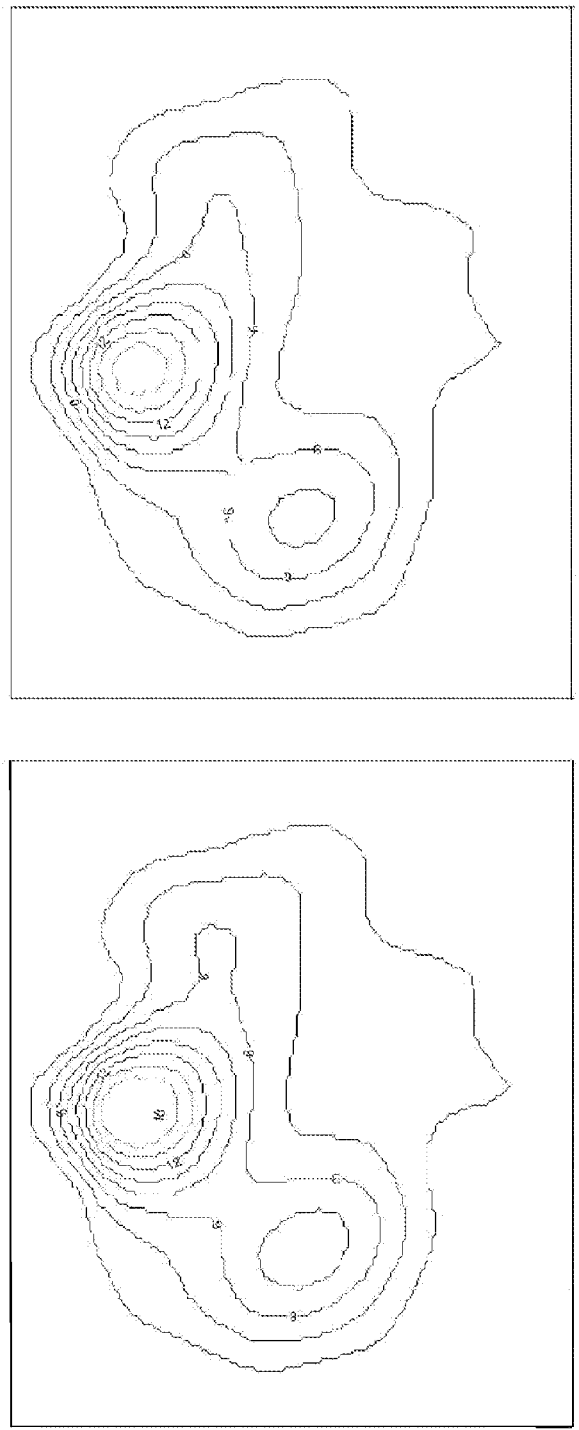
FIG. 11 is another view showing the changes in the impedance distributions in the section plane through the thorax in the form of contour lines at consecutive times following the administration of the bolus.
Figure 13:
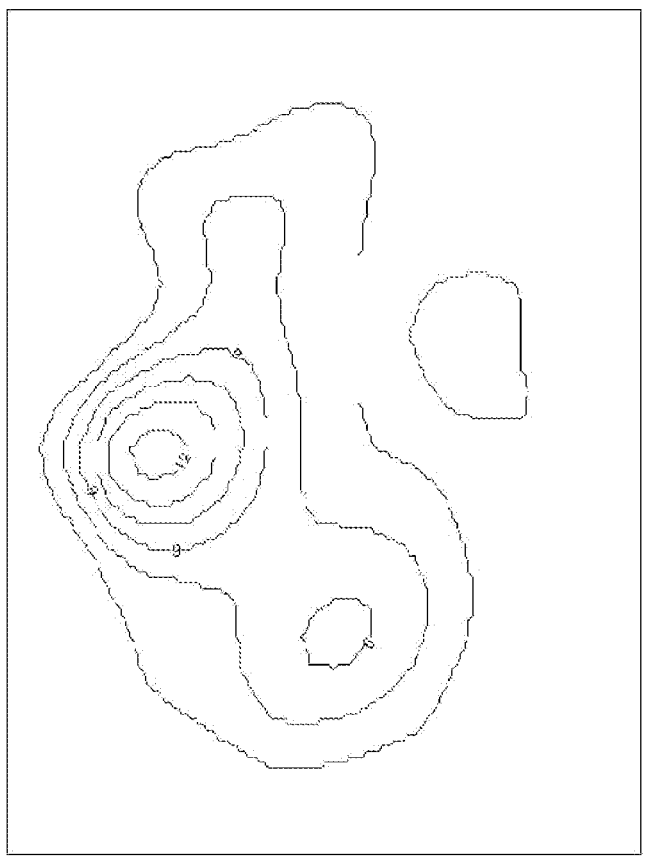
FIG. 13 is a view showing the impedance distributions in the section plane through the thorax in the form of contour lines at another time following the administration of the bolus.

FIG. 7 shows diagrams of lung perfusion by means of EIT as contour lines resolved at the times of 5.025 sec as well as 6.275 sec after bolus administration. The bolus is still fully distributed at 5.025 sec and begins to flow off again at 6.275 sec.

FIG. 8 shows diagrams of the lung perfusion by means of EIT as contour lines resolved at the time of 8.775 sec after bolus administration and 10.025 sec after bolus administration. The bolus flows off again from the lung through the heart.

FIG. 9 through FIG. 13 show diagrams of lung perfusion by means of EIT as contour lines resolved between the times 11.275 sec and 21.275 sec after bolus administration. The bolus flows out of the lung again through the heart. A heart beat can also be recognized here on the basis of the contour lines in the cardiac region.

While specific embodiments of the invention have been shown and described in detail to illustrate the application of the principles of the invention, it will be understood that the invention may be embodied otherwise without departing from such principles.

The invention claimed is:

1. A device for determining a regional distribution of a parameter for lung perfusion in a section plane of the thorax, the device comprising:
    an electrical impedance tomography unit comprising a plurality of electrodes, which can be placed on the thorax distributed around a circumference of the section plane, and a control and analysis unit, which is connected with the plurality of electrodes and is configured to consecutively feed alternating current or alternating voltage to each pair of electrodes to record voltage or current signals of other of the plurality of electrodes as measured signals and to reconstruct an impedance distribution in the section plane from the measured signals;
    an administering device for intravenous administration of a conductivity contrast medium, wherein:
    the control and analysis unit is further configured to display changes in the impedance distribution occurring as a consequence of the intravenous administration of conductivity contrast medium as a parameter for lung perfusion in the section plane as a function of time;

the administering device has a controllable dispensing device and the control and analysis unit and the controllable dispensing device are connected with one another via a data link and are configured to make available at least a start time and an end time and a quantity of an administered bolus of the conductivity contrast medium to the control and analysis unit, the control and analysis unit being configured to actuate the controllable dispensing device to administer a bolus of the conductivity contrast medium at a preset start time, in a preset quantity and with a preset time course via the data link, the controllable dispensing device being configured to send data concerning the start time, quantity and time course of the intravenous administration of a bolus to the control and analysis unit via the data link if the controllable dispensing device is triggered to administer a bolus directly or by an external device, the control and analysis unit being further configured to repeat the intravenous administration of the bolus of the conductivity contrast medium at preset time intervals and to display the changes of the parameter of the lung perfusion over time as a function of the time as a trend graph.

2. A device in accordance with claim 1, wherein the control and analysis unit and/or the controllable dispensing device is further configured to trigger the intravenous administration of the bolus of the conductivity contrast medium repeatedly upon repeated manual actuation of a switch by a user and to display the changes in the parameter of the lung perfusion over time as a function of time as a trend graph.

3. A device in accordance with claim 1, wherein at least one of the control and analysis unit and the controllable dispensing device is configured to be triggered by a signal fed by one or more external devices via an external device data link to administer the bolus of the conductivity contrast medium.

4. A device in accordance with claim 1, wherein the control and analysis unit is further configured to display the parameter for the perfusion spatially over the lung surface in the section plane through the thorax two-dimensionally.

5. A device in accordance with claim 1, wherein the control and analysis unit is further configured to determine surfaces in which the parameter for perfusion is above a preset threshold as a perfused surface in the section plane and to display perfused surfaces that arise from the intravenous administration of a bolus of the conductivity contrast medium as a trend graph as a function of the time of intravenous administrations of the boli of the conductivity contrast medium.

6. A device in accordance with claim 1, wherein the control and analysis unit is further configured to determine the regional distribution of ventilation in the section plane of the thorax during times without intravenous administration of conductivity contrast medium from the impedance distributions and to display the regional distribution of the ventilation in the section plane of the thorax as a function of time.

7. A device in accordance with claim 6, wherein the control and analysis unit is further configured to identify lung areas in which determined ventilation is above a preset threshold value and determined perfusion is below another, preset threshold value as dead spaces and to display the dead spaces in a shown tomogram of the lung.

8. A device in accordance with claim 7, wherein the control and analysis unit is further configured to display the changes in the dead spaces over time as a trend graph over a time period.

9. A device in accordance with claim 6, wherein the control and analysis unit is further configured to determine lung areas in which perfusion is above a preset threshold value and the ventilation is below another, preset threshold value as shunts and to display the shunts in a tomogram of the lung.

10. A device in accordance with claim 9, wherein the control and analysis unit is further configured to display the changes in dead spaces over time as a trend graph over a time period.

11. A device in accordance with claim 1, wherein:
the controllable dispensing device is provided with a temperature sensor for the conductivity contrast medium or with a temperature-regulating device for the conductivity contrast medium, which device can be controlled by the control and analysis unit; and
the control and analysis unit is configured to calibrate in absolute terms the cardiac output volume from determined or set temperature of the conductivity contrast medium on a basis of a dilution principle and the parameter for lung perfusion on the basis of the determined cardiac output volume.

12. A device in accordance with claim 11, wherein the control and analysis unit is further configured to at least one of:
determine a ratio of ventilation to perfusion spatially and to display the ratio of ventilation to perfusion; and
determine and display the ratio of ventilation to perfusion averaged over the lung area in the section plane of the thorax.

13. A device in accordance with claim 12, wherein the control and analysis unit is further configured to determine the ratio of ventilation to perfusion spatially and to store it in case of a plurality of consecutive intravenous administrations of boli and/or to determine the ratio of ventilation to perfusion averaged over the lung area in the section plane of the thorax and to store it and to display ratios of ventilation to perfusion together as a trend graph.

14. A device in accordance with claim 1, wherein the control and analysis unit is configured to monitor variables derived or calculated from determined lung perfusion, for preset criteria and to trigger an alarm when a determination is made that a preset criterion is not met any longer;
said control and analysis unit generates the impedance distribution as a function of the start time, the end time and the quantity.

15. A device for determining a regional distribution of a parameter for lung perfusion in a section plane of a thorax of a patient, the device comprising:
an electrical impedance tomography unit comprising a plurality of electrodes, which can be placed on the thorax, and distributed around a circumference of the section plane;
an administering device for selective intravenous administration of a plurality of boli of conductivity contrast medium to the patient at selectable and defined start times, defined end times and defined quantities;
a control and analysis unit connected to said plurality of electrodes, said control and analysis unit being configured to consecutively feed alternating current or alternating voltage to each pair of said electrodes to record voltage or current signals of other of the plurality of electrodes as measured signals and to reconstruct an impedance distribution in the section plane from the measured signals for each time window in which each of the boluses act, said control and analysis unit being further configured to display changes in the impedance distribution occurring as a consequence of intravenous administration of conductivity contrast medium as a parameter for lung perfusion in the section plane as a function of time;

a data link connecting said administering device and said control and analysis unit, said administering device and said control and analysis unit being configured to transmit the defined start time, end time, and quantity of each of the administered boli of the conductivity contrast medium to said control and analysis unit, said control and analysis unit being configured to have each impedance distribution correspond to the defined start time, end time and quantity.

16. A device in accordance with claim 15, wherein:
said control and analysis unit is configured to control the start time, the end time and the quantity of the conductivity contrast medium administered to the patient by said administering device.

17. A device in accordance with claim 16, wherein:
said control and analysis unit is configured to control the start time, the end time and the quantity of the conductivity contrast medium administered to the patient, said control and analysis unit is configured to generate the impedance distribution as a function of an outside device.

18. A device in accordance with claim 17, wherein:
said outside device is a respirator or monitor.

* * * * *